United States Patent [19]

Bigham

[11] Patent Number: 4,488,994
[45] Date of Patent: * Dec. 18, 1984

[54] BIS-ESTERS OF METHANEDIOL WITH PENICILLINS AND PENICILLANIC ACID 1,1-DIOXIDE

[75] Inventor: Eric C. Bigham, Chapel Hill, N.C.

[73] Assignee: Pfizer Inc., New York, N.Y.

[ * ] Notice: The portion of the term of this patent subsequent to Jan. 13, 1998 has been disclaimed.

[21] Appl. No.: 348,881

[22] Filed: Feb. 16, 1982

Related U.S. Application Data

[62] Division of Ser. No. 185,090, Sep. 8, 1980, Pat. No. 4,377,524, which is a division of Ser. No. 039,539, May 16, 1979, Pat. No. 4,244,951.

[51] Int. Cl.³ ............................................. C07D 499/32
[52] U.S. Cl. ................................. 260/239.1; 424/250; 424/211; 260/245.2 R
[58] Field of Search ...................................... 260/239.1

[56] References Cited

U.S. PATENT DOCUMENTS

| | | | |
|---|---|---|---|
| 3,838,152 | 9/1974 | Hou et al. ........................ | 260/239.1 |
| 3,850,908 | 11/1974 | Von Daehne et al. .......... | 260/239.1 |
| 3,869,449 | 3/1975 | Godtfredsen .................... | 260/239.1 |
| 3,981,865 | 9/1976 | Saikawa et al. .................. | 260/239.1 |
| 4,051,126 | 9/1977 | Murakami et al. ............... | 260/239.1 |
| 4,234,579 | 11/1980 | Barth ................................. | 424/246 |
| 4,244,951 | 1/1981 | Bigham ............................. | 424/250 |

FOREIGN PATENT DOCUMENTS

| | | |
|---|---|---|
| 2713683 | 10/1977 | Fed. Rep. of Germany . |
| 2824535 | 12/1978 | Fed. Rep. of Germany . |
| 1303491 | 1/1973 | United Kingdom . |
| 2044255 | 10/1980 | United Kingdom . |

*Primary Examiner*—Natalie Trousof
*Assistant Examiner*—Vera C. Clarke
*Attorney, Agent, or Firm*—Connolly and Hutz

[57] ABSTRACT

6'-Acylaminopenicillanoyloxymethyl esters of penicillanic acid 1,1-dioxide are useful as antibacterial agents. The 6'-aminopenicillanoyloxymethyl ester, halomethyl esters, alkylsulfonyloxymethyl esters and arylsulfonyloxymethyl esters of penicillanic acid 1,1-dioxide are all useful intermediates for the aforesaid antibacterial agents.

1 Claim, No Drawings

BIS-ESTERS OF METHANEDIOL WITH PENICILLINS AND PENICILLANIC ACID 1,1-DIOXIDE

CROSS REFERENCE TO RELATED APPLICATIONS

This application is a divisional of co-pending application Ser. No. 185,090, filed Sept. 8, 1980, now U.S. Pat. No. 4,377,524, which in turn is a divisional of application Ser. No. 039,539, filed May 16, 1979, and now U.S. Pat. No. 4,244,951.

BACKGROUND OF THE INVENTION

This invention relates to new chemical compounds. More particularly it relates to new chemical compounds which are of value as antibacterial agents. These new antibacterial agents are bis-esters of methanediol, in which one hydroxy group of the methanediol has been esterified with the carboxy group of a 6-acylaminopenicillanic acid compound, and the other hydroxy group of the methanediol has been esterified with the carboxy group of penicillanic acid 1,1-dioxide.

In addition, this invention relates to the 6'-aminopenicillanoyloxymethyl ester, halomethyl esters, alkylsulfonyloxymethyl esters and arylsulfonyloxymethyl esters of penicillanic acid 1,1-dioxide. The latter compounds are useful intermediates to the antibacterial agents of this invention.

West German Offenlegungsschrift No. 2,824,535, published Dec. 14, 1978, and Iranian Pat. No. 19,601, granted July 12, 1978, disclose penicillanic acid 1,1-dioxide, and esters thereof readily hydrolyzable in vivo, as antibacterial agents and as betalactamase inhibitors. Penicillanic acid 1,1-dioxide and esters thereof readily hydrolyzable in vivo increase the antibacterial effectiveness of certain penicillin and cephalosporin compounds against certain bacteria.

Belgian Pat. No. 764,688, granted Mar. 23, 1971, discloses: (a) certain 6'-acylaminopenicillanoyloxymethyl 6-acylaminopenicillanates; (b) certain 6'-acylaminopenicillanoyloxymethyl 6-aminopenicillanates; (c) 6'-aminopenicillanoyloxymethyl 6-aminopenicillanate; and (d) chloromethyl 6-aminopenicillanate. U.S. Pat. No. 3,850,908 discloses chloromethyl esters of several natural, biosynthetic and semi-synthetic penicillin compounds.

The antibacterial agents of the present invention are efficiently absorbed from the gastrointestinal tract of mammals, and after absorption they are transformed into a 6-acylaminopenicillanic acid and penicillanic acid 1,1-dioxide.

SUMMARY OF THE INVENTION

This invention provides new antibacterial agents of the formula

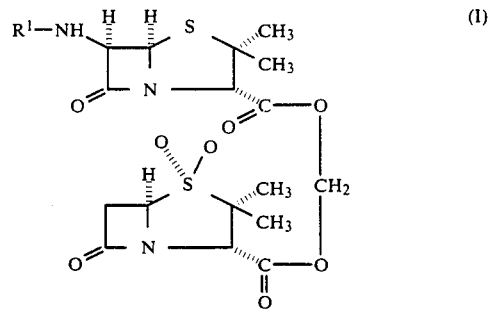

and the pharmaceutically-acceptable salts thereof, wherein $R^1$ is an acyl group of an organic carboxylic acid. However, preferred compounds of the formula I are those in which $R^1$ is an acyl group known from a natural, biosynthetic or semisynthetic penicillin compound. Especially preferred compounds of the formula I are those in which $R^1$ is selected from the group consisting of 2-phenylacetyl, 2-phenoxyacetyl, 2-amino-2-phenylacetyl, 2-amino-2-[4-hydroxyphenyl]acetyl, 2-carboxy-2-phenylacetyl, 2-carboxy-2-[2-thienyl]acetyl, 2-carboxy-2-[3-thienyl]acetyl, 2-[4-ethyl-2,3-dioxopiperazinocarbonylamino]-2-phenylacetyl and a group of the formula

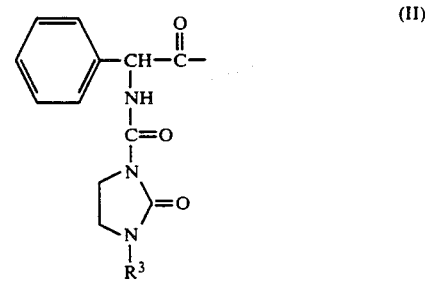

wherein $R^3$ is selected from the group consisting of hydrogen, alkanoyl having from two to four carbons and alkylsulfonyl having from one to three carbons.

Preferred individual compounds of formula I are:
6'-(2-phenylacetamido)penicillanoyloxymethyl penicillanate 1,1-dioxide,
6'-(2-phenoxyacetamido)penicillanoyloxymethyl penicillanate 1,1-dioxide,
6'-(2-amino-2-phenylacetamido)penicillanoyloxymethyl penicillanate 1,1-dioxide and
6-(2-amino-2-[4-hydroxyphenyl]acetamido)penicillanoyloxymethyl penicillanate 1,1-dioxide.

This invention also provides compounds of the formula:

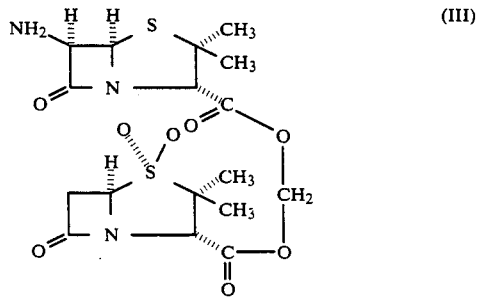

-continued
and

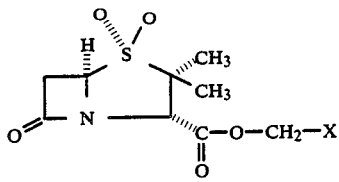 (IV)

and the salts thereof, wherein X is a good leaving group. Examples of X are chloro, bromo, iodo, alkylsulfonyloxy having from one to four carbon atoms, benzenesulfonyloxy and toluenesulfonyloxy. The compounds of formulae III and IV are useful as intermediates to the antibacterial agents of the invention.

DETAILED DESCRIPTION OF THE INVENTION

This invention relates to derivatives of penicillanic acid, which is represented by the following structural

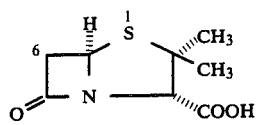 (V)

In formula V, broken line attachment of a substituent to the bicyclic nucleus indicates that the substituent is below the plane of the bicyclic nucleus. Such a substituent is said to be in the alpha-configuration. Conversely, solid line attachment of a substituent to the bicyclic nucleus indicates that the substituent is attached above the plane of the nucleus. This latter configuration is referred to as the beta-configuration.

Using this system, the compounds of formulae I and III are named as derivatives of penicillanoyloxymethyl penicillanate (VA), in which primed and unprimed locants are used to distinguish between the two ring systems, viz:

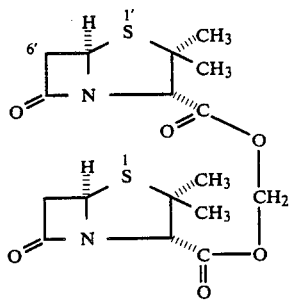 (VA)

Additionally, throughout this specification, whenever reference is made to a compound which has a 2-amino-2-(substituted)acetamido or 2-(substituted amino)-2-(substituted)acetamido group at the 6-position of a penicillanic acid derivative, it is to be understood that this refers to a compound in which said 2-amino-2-(substituted)acetamido or 2-(substituted amino)-2-(substituted)acetamido has the D-configuration.

In one method according to the invention a compound of formula I can be prepared by reacting a carboxylate salt of the formula

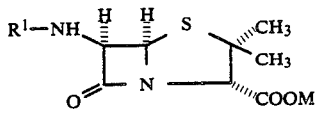 (VI)

with a compound of the formula

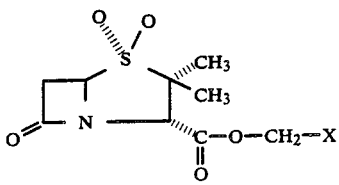 (VII)

wherein $R^1$ and X are as previously defined, and M is a carboxylate salt forming cation. A variety of cations can be used to form the carboxylate salt in the compound of formula VI, but salts which are commonly used include: alkali metal salts, such as sodium and potassium salts; alkaline earth metal salts, such as calcium and barium salts; and tertiary amine salts, such as trimethylamine, triethylamine, tributylamine, diisopropylethylamine, N-methylmorpholine, N-methylpiperidine, N-methylpyrrolidine, N,N'-dimethylpiperazine and 1,2,3,4-tetrahydroquinoline.

The reaction between a compound of formula VI and a compound of formula VII is usually carried out by contacting the reagents in a polar, organic solvent, at a temperature in the range from about 0° to about 80° C., and preferably from 25° to 50° C. The compounds of formula VI and VII are usually contacted in substantially equimolar proportions, but an excess of either reagent, for example up to a ten-fold excess, can be used. A wide variety of solvents can be used, but it is usually advantageous to use a relatively polar solvent, since this has the effect of speeding up the reaction. Typical solvents which can be used include N,N-dimethylformamide, N,N-dimethylacetamide, N-methylpyrrolidone, dimethylsulfoxide and hexamethylphosphoramide. The reaction time varies according to a number of factors, but at about 25° C. reaction times of several hours, e.g. 12 to 24 hours, are commonly used. When X is chloro or bromo, it is sometimes advantageous to add up to about one molar equivalent of an alkali metal iodide, which has the effect of speeding up the reaction.

The compound of formula I is isolated in conventional fashion. When a water-miscible solvent is used, it is usually sufficient simply to dilute the reaction medium with an excess of water. The product is then extracted into a water immiscible solvent, such as ethyl acetate, and then the product is recovered by solvent evaporation. When a water immiscible solvent is used, it is usually sufficient to wash the solvent with water, and then recover the product by solvent evaporation. The compound of formula I can be purified by well-known methods, such as recrystallization or chromatography, but due regard must be given to the lability of the beta-lactam ring system.

When the group $R^1$ in a compound of formula VI contains a basic group, such as a primary amino group, this group can interfere during the reaction with the ester VII. In this case it is usually advantageous to protect the amino group in $R^1$ before contacting the compound of formula VI with the compound of formula VII. A variety of conventional amino protecting groups can be used for this purpose. The only requirements for such a group are that: (a) it can be affixed to the compound of formula VI under conditions which do not adversely affect the compound of formula VI; (b) it is stable under the conditions under which the compound of formula VI reacts with the compound of formula VII; and (c) it can be removed after the reaction with the compound of formula VII is complete, using conditions which do not adversely affect the compound of formula I. Typical amino protecting groups which can be used are benzyloxycarbonyl, substituted benzyloxycarbonyl, 2-nitrophenylsulfenyl and 2,2,2-trichloroethoxycarbonyl. Benzyloxycarbonyl and 4-nitrobenzyloxycarobnyl are particularly convenient groups.

When the group $R^1$ in a compound of formula VI contains a carboxy group, it is usual to protect this carboxy group before the reaction with the compound of formula VII, particularly when the carboxy group is subject to ready decarboxylation. In this case it is advantageous to start with a compound of formula VI in which the carboxy group in $R^1$ is in the form of a readily hydrolyzable ester, e.g. a phenyl or substituted phenyl ester. After the coupling with the compound of formula VII is complete, the free carboxy group in $R^1$ is liberated by mild, alkaline hydrolysis, e.g. using the technique disclosed in U.S. Pat. No. 3,679,801. This methodology is especially useful when $R^1$ is a group such as 2-carboxy-2-phenylacetyl, 2-carboxy-2-[thienyl]acetyl, etc.

A variation of the foregoing method of preparing a compound of formula I involves reaction of a compound of the formula

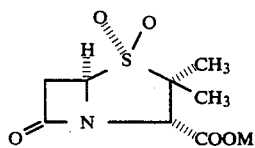

(VIII)

with a compound of the formula

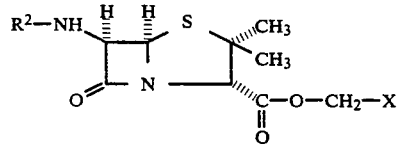

(IX)

wherein M and X are as defined previously, and $R^2$ is the group $R^1$, but with any free amino groups and/or carboxy groups protected, followed if necessary by removal of any amino or carboxy protecting group. In the compounds of formula IX, the free amino groups and the carboxy groups are protected with exactly the same protecting groups as described earlier for the compound of formula VI. The reaction between a compound of formula VIII and IX is carried out in exactly the same manner that is used for the reaction of a compound of formula VI with a compound of formula VII. Finally, any amino and/or carboxy protecting groups are removed, and these are removed in conventional manner for the group involved.

In another method according to the invention, a compound of formula I can be prepared by acylation of the compound of formula III with an activated derivative of an acid of the formula $R^2$-COOH, wherein $R^2$ is as previously defined, followed if necessary by removal of any amino and/or carboxy protecting groups from $R^2$. This converts the moiety $R^2$-CO into the moiety $R^1$-CO.

The acylation reaction is usually conducted in a reaction-inert solvent system. In a typical acylation procedure, from about 0.5 to about three molar equivalents of the activated derivative of the acid of formula $R^2$-COOH is contacted with the compound of formula III, in a reaction-inert solvent system, at a temperature in the range from about $-40°$ to about $30°$ C., and preferably from about $-10°$ to about $10°$ C. The preferred ratio of activated derivative to compound of formula III is 1.0:1.0 to 1.2:1.0. Reaction-inert solvents which are commonly used in this acylation are: chlorinated hydrocarbons, such as chloroform and dichloromethane; ethers, such as diethyl ether and tetrahydrofuran; low molecular weight esters, such as ethyl acetate and butyl acetate; low molecular weight aliphatic ketones, such as acetone and methyl ethyl ketone; tertiary amides, such as N,N-dimethylformamide and N-methylpyrrolidone; acetonitrile; water; and mixtures thereof. When aqueous or partially aqueous solvent systems are used, the pH should be maintained in the range from about 4 to about 9, and preferably about 7.

An activated derivative of the acid of the formula $R^2$-COOH which is commonly used is an acid halide, e.g. the acid chloride. In this instance it is preferable, though not essential, to carry out the acylation in the presence of an acid binder. Suitable acid binders are tertiary amines such as trialkylamines, e.g. triethylamine, N-methylmorpholine, N,N-dimethylaniline, pyridine and the like, or bicarbonates such as potassium bicarbonate or sodium bicarbonate. Buffer systems such as phosphate buffers can also be used.

Other activated derivatives of the acid of formula $R^2$-COOH which can be used are active esters. Examples of active esters are phenyl esters, such as 4-nitrophenyl and 2,4,5-trichlorophenyl esters; thio esters, such as thiol methyl and thiol phenyl esters; and N-hydroxy esters, such as N-hydroxysuccinimide and N-hydroxyphthalimide esters. These active esters are prepared by methods well-known in the art. In many cases, the active ester can be replaced by the corresponding acid azide, or by the imidazole or triazole amide.

Another method for activation of the acid of formula $R^2$-COOH involves mixed anhydride formation, i.e. mixed carboxylic-carbonic and mixed dicarboxylic anhydride formation. In the case of mixed carboxylic carbonic anhydrides, a carboxylate salt of the acid of formula $R^2$-COOH is usually reacted with a lower-alkyl chloroformate, e.g. ethyl chloroformate; in the case of a mixed dicarboxylic anhydride, a carboxylate salt of the acid of formula $R^2$-COOH is usually reacted with a hindered lower-alkanoyl chloride, e.g. pivaloyl chloride.

In addition to the above, the acid of formula $R^2$-COOH can be activated by contacting the acid with a peptide coupling agent, according to standard procedures. Such agents include carbodiimides, for example dicyclohexylcarbodiimide, alkoxyacetylenes, for example methoxyacetylene and ethoxyacetylene, and N-ethoxycarbonyl-2-ethoxy-1,2-dihydroquinoline.

The protecting groups used to protect amino or carboxy groups in a compound of formula $R^2$-COOH are those conventionally used during acylation of a 6-aminopenicillanic acid derivative. Protecting groups which are particularly useful for amino groups are the benzyloxycarbonyl group, the 4-nitrobenzyloxycarbonyl group and the enamines formed by condensation with a beta-dicarbonyl compound such as an alkyl acetoacetate. After the acylation step, the amino protecting group is removed in conventional fashion. When the acid of formula $R^2$-COOH is to be activated as an acid halide e.g. acid chloride, an especially convenient manner of protecting an amino group involves salt formation, e.g. formation of a hydrochloride salt.

The compounds of formula VI are known antibiotics, which are prepared by the published procedures.

The compounds of formula VII are prepared from the compounds of formula VIII by reaction with a compound of formula Y-$CH_2$-X, wherein X and Y are each good leaving groups, e.g. chloro, bromo, iodo, alkylsulfonyloxy, benenesulfonyloxy or toluenesulfonyloxy. The same conditions that were described previously for reaction of a compound of formula VII with a compound of formula VI are used for this reaction, except that it is preferable to use an excess of the compound of formula X-$CH_2$-Y (e.g. a four-fold excess).

In like manner, the compounds of formula IX are prepared by reaction of a compound of formula

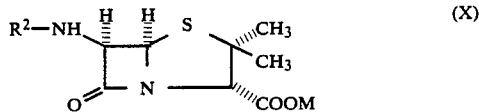 (X)

with a compound of formula Y-$CH_2$-X, wherein $R^2$, M, Y and X are as previously defined. The conditions used are the same as those described previously for reaction of a compound of formula VIII with a compound of formula X-$CH_2$-Y.

The compound of formula III can be prepared by a three-step procedure which comprises: (a) conversion of 6-aminopenicillanic acid into a 6-(protected amino)-penicillanic acid; (b) reaction of a salt of the 6-(protected amino)penicillanic acid with a compound of formula VII; and (c) removal of the amino protecting group A wide variety of amino protecting groups can be used for this purpose, and typical examples are benzyloxycarbonyl, 4-nitrobenzyloxycarbonyl and 2,2,2-trichloroethoxycarbonyl. Steps (a) and (c) are carried out in conventional fashion, and step (b) is carried out in exactly the same manner that was described previously for reaction of a compound of formula VII with a compound of formula VI.

Alternatively, the compound of formula III can be prepared by a four-step procedure which comprises (i) conversion of 6-aminopenicillanic acid into a 6-(protected amino)penicillanic acid; (ii) reaction of a salt of the 6-(protected amino)penicillanic acid with a compound of formula X-$CH_2$-Y, wherein X and Y are as previously defined; (iii) reaction of the product of step (ii) with a compound of formula VIII; and (iv) removal of the amino protecting group. A wide variety of amino protecting groups can be used for this purpose, and typical examples are benzyloxycarbonyl, 4-nitrobenzyloxycarbonyl and 2,2,2-trichloroethoxycarbonyl. Steps (i) and (iv) are carried out in conventional fashion; step (ii) is carried out in exactly the same manner that was described previously for reaction of a compound of formula VIII with a compound of formula X-$CH_2$-Y; and step (iii) is carried out in exactly the same manner that was described previously for reaction of a compound of formula VI with a compound of formula VII.

Penicillanic acid 1,1-dioxide and the salts thereof are prepared by published procedures (see West German Offenlegungsschrift No. 2,824,535).

Those compounds of formula I which have a basic function, e.g. an amino group, in the group $R^1$ will form acid addition salts, and these acid addition salts are considered to be within the scope and purview of this invention. Said acid addition salts are prepared by standard methods for penicillin compounds, for example by combining a solution of the compound of formula I in a suitable solvent (e.g. water, acetone, methanol, ethanol or butanol) with a solution containing a stoichiometric equivalent of the appropriate acid. If the salt precipitates, it is recovered by filtration. Alternatively, it can be recovered by evaporation of the solvent, or, in the case of aqueous solutions, by lyophilization. Of particular value are the sulfate, hydrochloride, hydrobromide, nitrate, phosphate, citrate, tartrate, pamoate, perchlorate, sulfosalicylate and 4-toluenesulfonate salts.

Those compounds of formula I which have an acidic function, e.g. a carboxyl group, in the group $R^1$ will form base salts, and these base salts are to be considered within the scope and purview of this invention. The base salts are prepared by standard methods for penicillin compounds, for example by contacting the acidic and basic components in a stoichiometric ratio, in an aqueous, non-aqueous or partially aqueous medium, as appropriate. They are then recovered by filtration, by precipitation with a non-solvent followed by filtration, by evaporation of the solvent, or, in the case of aqueous solutions, by lyophilization, as appropriate. Basic agents which are suitably employed in salt formation belong to both the organic and inorganic types, and they include ammonia, organic amines, alkali metal hydroxides, carbonates, bicarbonates, hydrides and alkoxides, as well as alkaline earth metal hydroxides, carbonates, hydrides and alkoxides. Representative examples of such bases are primary amines, such as n-propylamine, n-butylamine, aniline, cyclohexylamine, benzylamine, p-toluidine and octylamine; secondary amines, such as diethylamine, N-methylaniline, morpholine, pyrrolidine and piperidine; tertiary amines, such as triethylamine, N,N-dimethylaniline, N-ethylpiperidine, N-methylmorpholine and 1,5-diazabicyclo[4.3.0]non-5-ene; hydroxides, such as sodium hydroxide, potassium hydroxide, ammonium hydroxide and barium hydroxide; alkoxides, such as sodium ethoxide and potassium ethoxide; hydrides, such as calcium hydride and sodium hydride; carbonates, such as potassium carbonate and sodium carbonate; and bicarbonates, such as sodium bicarbonate and potassium bicarbonate.

When contemplating therapeutic use for a salt of an antibacterial compound of this invention, it is necessary to use a pharmaceutically-acceptable salt; however, salts other than these can be used for a variety of purposes. Such purposes include isolating and purifying particular compounds, and interconverting pharmaceutically-acceptable salts and their non-salt counterparts.

The compounds of formula I possess in vivo antibacterial activity in mammals, and this activity can be demonstrated by standard techniques for penicillin compounds. For example, the compound of formula I is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compound is assessed by counting the number of survivors which have been challenged by the bacterium and also have received the compound of formula I. The compounds of formula I can be administered by both the oral (p.o.) and subcutaneous (s.c.) route.

The in vivo activity of the antibacterial compounds of this invention makes them suitable for the control of bacterial infections in mammals, including man, by both the oral and parenteral modes of administration. The compounds are useful in the control of infections caused by susceptible bacteria in human subjects. In general, it is the substitutent $R^1$ which determines whether a given bacterium will be susceptible to a given compound of formula I. A compound of formula I breaks down to the corresponding compound of formula VI (or free acid thereof) and penicillanic acid 1,1-dioxide after administration to a mammalian subject by both the oral and parenteral route. Penicillanic acid 1,1-dioxide then functions as a beta-lactamase inhibitor, and it increases the antibacterial effectiveness of the compound of formula VI (or free acid thereof). For example, when $R^1$ is 2-phenylacetyl or 2-phenoxyacetyl, the compounds will find use in the control of infections caused by susceptible strains of *Staphylococcus aureus;* when $R^1$ is D-2-amino-2-phenylacetyl, D-2-amino-2-[4-hydroxyphenyl]acetyl, 2-carboxy-2-phenylacetyl, 2-carboxy-2-[2-thienyl]acetyl, 2-carboxy-2-[3-thienyl]acetyl, 2-[4-ethyl-2,3-dioxopiperazinocarbonylamino]-2-phenylacetyl or a group of formula II, the compounds are useful in the control of infections caused by susceptible strains of *Escherichia coli.*

In determining whether a particular strain of *Staphylococcus aureus* or *Escherichia coli* is sensitive to a particular compound of formula I, the in vivo test described earlier can be used. Alternatively, the minimum inhibitory concentration (MIC) of a 1:1 mixture of the compound of formula VI (or its corresponding free acid) and the compound of formula VIII (or its corresponding free acid) can be measured. The MIC's can be measured by the procedure recommended by the International Collaborative Study on Antibiotic Sensitivity Testing (Ericcson and Sherris, *Acta. Pathologica et Microbiologia* Scandinav, Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye.

When using an antibacterial compound of this invention, or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The compounds of this invention will normally be used orally at dosages in the range from about 20 to about 100 mg. per kilogram of body weight per day, and parenterally at dosages from about 10 to about 100 mg. per kilogram of body weight per day, usually in divided doses. In some instances it may be necessary to use doses outside these ranges.

The following examples and preparations are provided solely for further illustration. Infrared (IR) spectra were measured as potassium bromide discs (KBr discs) and diagnostic absorption bands are reported in wave numbers (cm$^{-1}$). Nuclear magnetic resonance spectra (NMR) were measured at 60 MHz for solutions in deuterated chloroform (CDCl$_3$) or deuterated dimethyl sulfoxide (DMSO-d$_6$), and peak positions are reported in parts per million downfield from tetramethylsilane. The following abbreviations for peak shapes are used: s, singlet; d, doublet; t, triplet; q, quartet, m, multiplet.

EXAMPLE 1

6'-(2-Phenylacetamido)penicillanoyloxymethyl Penicillanate 1,1-Dioxide

To a stirred solution of 1.3 g. of potassium 6-(2-phenylacetamido)penicillanate in 20 ml. of dimethyl sulfoxide was added 845 mg. of chloromethyl penicillanate 1,1-dioxide followed by a few milligrams of sodium iodide. Stirring was continued overnight at ca. 25° C., and then the reaction mixture was poured into 140 ml. of ice-water. The pH was raised to 8.5, and then the mixture was extracted with ethyl acetate. The combined ethyl acetate extracts were washed with water, dried (Na$_2$SO$_4$) and evaporated in vacuo. This afforded 600 mg. of crude material.

The crude material was chromatographed on silica gel, eluting with a 1:1 mixture of ethyl acetate and hexane, and this afforded 200 mg. of the title compound (12% yield). The IR spectrum (KBr disc) showed an absorption at 1783 cm$^{-1}$. The NMR spectrum (CDCl$_3$) showed absorptions at 7.4 (s), 6.3 (d), 5.9 (s), 5.8–5.3 (m), 4.65 (t), 4.45 (s), 3.65 (s), 3.45 (d), 1.62 (s) and 1.48–1.4 (m) ppm.

EXAMPLE 2

6'-(2-Phenoxyacetamido)penicillanoyloxymethyl Penicillanate 1,1-Dioxide

A mixture of 1.4 g. of potassium 6-(2-phenoxyacetamido)penicillanate, 845 mg. of chloromethyl penicillanate 1,1-dioxide, 20 ml. of dimethyl sulfoxide and a few milligrams of sodium iodide was stirred at ca. 25° C. overnight. The mixture was poured into 140 ml. of ice-water and the pH was adusted to 8.5. The resultant aqueous system was extracted with ethyl acetate, and the extracts were combined, washed with water, dried (Na$_2$SO$_4$) and evaporated in vacuo. This afforded 660 mg. of crude material.

The crude material was chromatographed on silica gel, using a 1:1 mixture of ethyl acetate and hexane as eluant, and this afforded 230 mg. of the title product (13% yield). The IR spectrum (KBr disc) showed an absorption at 1786 cm$^{-1}$. The NMR spectrum (CDCl$_3$) showed absorptions at 7.4 (s), 5.85 (s), 5.45 (s), 5.05 (s), 4.6 (t), 4.43 (s), 4.4 (s), 3.45 (d), 1.62 (s), 1.48 (s), 1.44 (s) and 1.4 (s) ppm.

EXAMPLE 3

6'-(2-Amino-2-phenylacetamido)penicillanoyloxymethyl Penicillanate 1,1-Dioxide

To a solution of 1.6 g. of 6'-(2-benzyloxycarbonylamino-2-phenylacetamido)penicillanoyloxymethyl penicillanate 1,1-dioxide in 100 ml. of tetrahydrofuran and 80 ml. of water was added 0.12 ml. of glacial acetic acid followed by 1.6 g. of 10% palladium-on-carbon. The mixture was shaken under an atmosphere of hydrogen at a pressure of ca. 50 psig for 1.5 hours. At this point the catalyst was removed by filtration and 1.6 g. of fresh catalyst was added. The mixture was shaken under hydrogen at ca. 50 psig for a further 1 hour. The catalyst was removed by filtration and the bulk of the tetrahydrofuran was removed by evaporation in vacuo. The pH of the residual aqueous phase was lowered to 2.0 using 6N hydrochloric acid and the acidified solution was extracted with ethyl acetate. The extracts were dried (Na$_2$SO$_4$) and evaporated in vacuo to give 500 mg. of impure starting material. The pH of the above acidified solution was raised to 8.5 and then it was further extracted with ethyl acetate. The latter extracts were combined, dried (Na$_2$SO$_4$) and evaporated in vacuo to give 500 mg. of the title compound (38% yield).

EXAMPLE 4

6'-(2-Benzyloxycarbonylamino-2-phenylacetamido)-penicillanoyloxymethyl Penicillanate 1,1-Dioxide To a stirred solution of 1.9 g. of potassium 6-(2-benzyloxycarbonylamino-2-phenylacetamido)penicillanate in 30 ml. of dimethyl sulfoxide was added 930 mg. of chloromethyl penicillanate 1,1-dioxide followed by a few milligrams of sodium iodide. Stirring was continued at ambient temperature overnight, and then the reaction mixture was poured into 60 ml. of water. The pH was raised to 8.5 and the product was extracted into ethyl acetate. The extracts were washed with water and with saturated sodium chloride solution, and then they were dried (Na$_2$SO$_4$). Evaporation of the ethyl acetate in vacuo gave 800 mg. of crude product.

The crude product was purified by chromatography on silica gel, using 1:1 ethyl acetate-hexane as eluant, to give 440 mg. of the title compound (18% yield). The NMR spectrum of the product (CDCl$_3$) showed absorptions at 7.4 (m, 10H), 7.1 (d, 1H, J=8 Hz), 6.2 (d, 1H, J=8 Hz), 5.9 (s, 2H), 5.7–5.2 (m, 3H), 5.1 (s, 2H), 4.6 (t, 1H), 4.4 (s, 2H), 3.4 (d, 2H) and 1.7–1.2 (m, 12H) ppm.

EXAMPLE 5

6'-(2-Amino-2-phenylacetamido)penicillanoyloxymethyl Penicillanate 1,1-Dioxide

6'-(2-[4-Nitrobenzyloxycarbonylamino]-2-phenylacetamido)penicillanoyloxymethyl penicillanate 1,1-dioxide was hydrogenated in the presence of 10% palladium-on-carbon, according to the procedure of Example 3. After the hydrogenation, the catalyst was removed by filtration and the pH was raised to 8.5. The resulting mixture was extracted with ethyl acetate, and then the extracts were combined, dried using sodium sulfate and evaporated in vacuo. The residue was dissolved in 3 ml. of ethyl acetate, and the resulting solution was added dropwise to 40 ml. of hexane. The solid which precipitated was recovered by filtration to give 500 mg. of crude product.

The crude product was purified by chromatography on silica gel, using ethyl acetate as eluant, to give a 40% yield of the title compound. The IR spectrum (KBr disc) showed an absorption at 1802 cm$^{-1}$. The NMR spectrum (CDCl$_3$) showed absorptions at 8.1 (d, 1H, J=6 Hz), 7.4 (s, 4H), 5.9 (q, 2H), 5.7–5.5 (m, 2H), 4.75–4.6 (m, 2H), 4.55 (s, 1H), 4.45 (s, 1H), 3.55 (d, 2H), 1.6 (d, 6H) and 1.5 (d, 6H) ppm.

EXAMPLE 6

6'-(2-[4-Nitrobenzyloxycarbonylamino]-2-phenylacetamido)penicillanoyloxymethyl Penicillanate 1,1-Dioxide The title compound was prepared from potassium 6-(2-[4-nitrobenzyloxycarbonylamino]-2-phenylacetamido)penicillanate and chloromethyl penicillanate 1,1-dioxide using the procedure of Example 4, except that the reaction mixture was heated at 45° C. for 3 hours after being allowed to stir overnight at ambient temperature. After chromatography on silica gel, a 24% yield of product was obtained. The NMR spectrum (CDCl$_3$) showed absorptions at 8.2 (d, 2H, J=8 Hz), 7.7–7.4 (m, 7H), 6.9 (d, 2H, J=8 Hz), 5.9 (s, 2H), 5.8–5.3 (m, 3H), 5.2 (s, 2H), 4.7 (t, 1H), 4.5 (s, 2H), 3.5 (d, 2H) and 1.7–1.4 (m, 12H) ppm.

EXAMPLE 7

6'-(2-Amino-2-[4-Hydroxyphenyl]acetamido)penicillanoyloxymethyl Penicillanate 1,1-Dioxide To a solution of 700 mg. of 6'-(2-[4-nitrobenzyloxycarbonylamino]-2-[4-hydroxyphenyl]acetamido)-penicillanoyloxymethyl penicillanate 1,1-dioxide in 25 ml. of water and 35 ml. of tetrahydrofuran was added 700 mg. of 10% palladium-on-carbon. This mixture was shaken under an atmosphere of hydrogen at ca. 50 psig for 70 minutes. The catalyst was removed by filtration and then the bulk of the tetrahydrofuran was removed by evaporation in vacuo. The remaining aqueous phase was basified to pH 8.5, and then it was extracted with ethyl acetate. The extracts were washed with water and with saturated sodium chloride solution, and then they were dried (Na₂SO₄) and evaporated in vacuo. The residue was dissolved in 3 ml. of ethyl acetate, and this solution was added dropwise to an excess of hexane. The solid which precipitated was recovered by filtration and dried to give 300 mg. of the title compound (56% yield).

The above product was combined with additional material of similar purity and chromatographed on silica gel using ethyl acetate as the eluant. The appropriate column fractions were combined and evaporated in vacuo, and the residue was dissolved in a small volume of ethyl acetate. The latter solution was then added dropwise to an excess of hexane, and the solid which precipitated was recovered by filtration. The IR spectrum (KBr disc) of the material so obtained showed an absorption at 1786 cm$^{-1}$. The NMR spectrum (CDCL₃/DMSO-d₆) showed absorptions at 7.4–6.6 (m, 4H), 5.9 (s, 1H), 5.8–5.4 (m, 2H), 4.8–4.3 (m, 4H), 3.5 (d, 2H) and 1.5 (m, 12H) ppm.

EXAMPLE 8

6'-(2-[4-Nitrobenzyloxycarbonylamino]-2-[4-hydroxyphenyl]acetamido)penicillanoyloxymethyl Penicillanate 1,1-Dioxide A solution of 7.0 g. of potassium 6-(2-[4-nitrobenzyloxycarbonylamino]-2-[4-hydroxyphenyl]acetamido)penicillanate and 3.0 g. of chloromethyl penicillanate 1,1-dioxide in 40 ml. of dimethyl sulfoxide was heated at 45° C. for 4.5 hours. The solution was then poured into 120 ml. of water and the pH was adjusted to 8.5. The resulting mixture was extracted with ethyl acetate, and the combined extracts were washed with water and with saturated sodium chloride solution and then they were dried (Na₂SO₄). The dried solution was evaporated in vacuo to give 2.0 g. of crude product.

The crude product was purified by chromatography on silica gel using 1.5:1 ethyl acetate-hexane as eluant. This afforded 720 mg. (9% yield) of material which showed only a single spot when assayed by thinlayer chromatography.

EXAMPLE 9

The procedure of Example 1 is repeated, except that the potassium 6-(2-phenylacetamido)penicillanate is replaced by:
potassium 6-(2-[4-ethyl-2,3-dioxopiperazinocarbonylamino]-2-phenylacetamido)penicillanate,
potassium 6-(2-[2-oxoimidazolidinocarbonylamino]2-phenylacetamido)penicillanate,
potassium 6-(2-[3-acetyl-2-oxoimidazolidinocarbonylamino]-2-phenylacetamido)penicillanate,
potassium 6-(2-[3-butyryl-2-oxoimidazolidinocarbonylamino]-2-phenylacetamido)penicillanate,
potassium 6-(2-[3-methylsulfonyl-2-oximidazolidinocarbonylamino]-2-phenylacetamido)penicillanate and
potassium 6-(2-[3-isopropylsulfonyl-2-oxoimidazolidinocarbonylamino]-2-phenylacetamido)penicillanate,
respectively. This affords:
6'-(2-[4-ethyl-2,3-dioxopiperazinocarbonylamino]-2-phenylacetamido)penicillanoyloxymethyl penicillanate 1,1-dioxide,
6'-(2-[2-oxoimidazolidinocarbonylamino]-2-phenylacetamido)penicillanoyloxymethyl penicillanate 1,1-dioxide,
6'-(2-[3-acetyl-2-oxoimidazolidinocarbonylamino]-2-phenylacetamido)penicillanoyloxymethyl penicillanate 1,1-dioxide,
6'-(2-[3-butyryl-2-oxoimidazolidinocarbonylamino]-2-phenylacetamido)penicillanoyloxymethyl penicillanate 1,1-dioxide,
6'-(2-[3-methylsulfonyl-2-oxoimidazolidinocarbonylamino]-2-phenylacetamido)penicillanoyloxymethyl penicillanate 1,1-dioxide and
6'-(2-[3-isopropylsulfonyl-2-oxoimidazolidinocarbonylamino]-2-phenylacetamido)penicillanoyloxymethyl penicillanate 1,1-dioxide, respectively.

EXAMPLE 10

The procedure of Example 2 is repeated, except that the chloromethyl penicillanate 1,1-dioxide used therein is replaced by an equimolar amount of:
bromomethyl penicillanate 1,1-dioxide,
iodomethyl penicillanate 1,1-dioxide,
methylsulfonyloxymethyl penicillanate, 1,1-dioxide,
isobutylsulfonyloxymethyl penicillanate 1,1-dioxide,
benzenesulfonyloxymethyl penicillanate 1,1-dioxide and
4-toluenesulfonyloxymethyl penicillanate 1,1-dioxide, respectively. In each case, this affords 6'-(2-phenoxyacetamido)penicillanoyloxymethyl penicillanate 1,1-dioxide.

EXAMPLE 11

6'-(2-Benzyloxycarbonylamino-2-phenylacetamido)penicillanoyloxymethyl Penicillanate 1,1-Dioxide A mixture of 570 mg. of chloromethyl 6-(2-benzyloxycarbonylamino-2-phenylacetamido)penicillanate, 324 mg. of sodium penicillanate 1,1-dioxide, a few milligrams of sodium iodide and 20 ml. of dimethyl sulfoxide was stirred at room temperature overnight. The reaction mixture was added to 80 ml. of water, and the pH was raised to 8.5. The product was extracted into ethyl acetate. The extract was washed with water and with saturated sodium chloride solution, and then it was dried (Na₂SO₄). Evaporation in vacuo then afforded 360 mg. of the title compound.

EXAMPLE 12

6'-(2-[4-Nitrobenzyloxycarbonylamino]-2-phenylacetamido)penicillanoyloxymethyl Penicillanate 1,1-Dioxide A mixture of 500 mg. of chloromethyl 6-(2-[4-nitrobenzyloxycarbonylamino]-2-phenylaetamido)-penicillanate, 245 mg. of sodium penicillanate 1,1-dioxide, a few milligrams of sodium iodide and 10 ml. of dimethyl sulfoxide was stirred at room temperature overnight. At this point, an additional 83 mg. of sodium penicillanate 1,1-dioxide was added. Stirring was continued for 4 hours, and then the reaction mixture was poured into water. The aqueous system was basified to pH 8.5, and then it was extracted with ethyl acetate. The extracts were combined, washed with water and with saturated sodium chloride solution, and then they were dried (Na₂SO₄). Evaporation in vacuo then afforded 430 mg. of the title compound, contaminated with some chloromethyl 6-(2-[4-nitrobenzyloxycarbonylamino]-2-phenylacetamido)penicillanate.

EXAMPLE 13

6'-(2-[4-Nitrobenzyloxycarbonylamino]-2-[4-hydroxyphenyl]-acetamido)penicillanoyloxymethyl Penicillanate 1,1-Dioxide A solution of 2.07 g. of chloromethyl 6-(2-[4-nitrobenzyloxycarbonylamino]-2-[4-hydroxyphenyl]acetamido)-penicillanate, 1.1 g. of sodium penicillanate 1,1-dioxide, and a few milligrams of sodium iodide in 30 ml. of dimethyl sulfoxide was maintained at 45° C. for 5 hours. The reaction mixture was added to 100 ml. of water and the pH was raised to 8.5. The product was extracted into ethyl acetate. The extracts were combined, washed with water and with saturated sodium chloride solution, and then they were dried ($Na_2SO_4$). Evaporation in vacuo then afforded 1.6 g. of crude product.

The crude product was chromatographed on silica gel using 1.5:1 ethyl acetate-hexane as eluant, to give 550 mg. (18% yield) of the title compound. The NMR spectrum ($CDCl_3$/DMSO-$d_6$) showed absorptions at 8.4 (d, 1H, J=8 Hz), 8.1 (d, 2H, J=8 Hz), 7.7–6.6 (m, 7H), 5.9 (s, 2H), 5.7–5.2 (m, 3H), 5.2 (s, 2H), 4.7 (t, 1H) 4.4 (d, 2H) and 1.5 (d, 12H) ppm.

EXAMPLE 14

Chloromethyl 6-(2-phenylacetamido)penicillanate and chloromethyl 6-(2-phenoxyacetamido)penicillanate are reacted with sodium penicillanate 1,1-dioxide, according to the procedure of Example 11. This affords:

6'-(2-phenylacetamido)penicillanoyloxymethyl penicillanate 1,1-dioxide
and
6'-(2-phenoxyacetamido)penicillanoyloxymethyl penicillanate 1,1-dioxide,
respectively.

EXAMPLE 15

6'-(2-Phenylacetamido)penicillanoyloxymethyl Penicillanate 1,1-Dioxide

To a stirred solution of 4.62 g. of 6'-aminopenicillanoyloxymethyl penicillanate 1,1-dioxide in 25 ml. of chloroform is added 1.50 ml. of triethylamine. The mixture is cooled to 0° C., and a solution of 1.55 g. of 2-phenylacetyl chloride in 10 ml. of chloroform is added dropwise at 0° C. The resulting mixture is stirred for 5 minutes at 0° C. and then for 30 minutes at 25° C. The solvent is removed by evaporation in vacuo and the residue is partitioned between ethyl acetate and water at pH 8. The ethyl acetate layer is removed, washed with water, dried ($Na_2SO_4$) and evaporated in vacuo, to give the title compound.

EXAMPLE 16

6'-(2-Phenoxyacetamido)penicillanoyloxymethyl Penicillanate 1,1-Dioxide

The title compound is prepared by acylation of 6'-aminopenicillanoyloxymethyl penicillanate 1,1-dioxide with 2-phenoxyacetyl chloride, according to the procedure of Example 15.

EXAMPLE 17

6'-(2-Amino-2-phenylacetamido)penicillanoyloxymethyl Penicillanate 1,1-Dioxide

To a stirred solution of 155.2 g. of potassium N-(1-methyl-2-ethoxycarbonylvinyl)-D-2-amino-2-phenylacetate hemihydrate (Chem. Ber., 98, 789 [1965]) in 2,000 ml. of ethyl acetate is added 2.5 ml. of N-methylmorpholine and 70 ml. of isobutyl chloroformate, at −15° C. Stirring is continued at −15° C. for 15 minutes, an then a solution of 231 g. of 6'-aminopenicillanoyloxymethyl penicillanate 1,1-dioxide in 1,000 ml. of ethyl acetate is added, dropwise, at −15° C., over a period of 15 minutes. Stirring is continued at 15° C. for 1 hour and then the reaction mixture is allowed to warm to room temperature. At this point the reaction mixture is washed with water, aqueous sodium bicarbonate (0.5M) and again with water. The ethyl acetate solution is then dried and evaporated in vacuo. The residue is dissolved in 2,000 ml. of 1:1 tetrahydrofuran-water and the pH is adjusted to 2.5. The solution is stirred at a pH of 2.5 for 1 hour, and then the bulk of the tetrahydrofuran is removed by evaporation in vacuo. The pH of the aqueous phase is adjusted to 8.5, and then the aqueous phase is extracted with ethyl acetate. The extracts are washed with water, dried ($Na_2SO_4$) and evaporated in vacuo to give the title compound.

EXAMPLE 18

6'-(2-Amino-2-[4-hydroxyphenyl]acetamido-penicillanoyloxymethyl Penicillanate 1,1-Dioxide The title compound is prepared from 6'-aminopenicillanoyloxymethyl penicillanate 1,1-dioxide and sodium N-(1-methyl-2-methoxycarbonylvinyl)-D-2-amino-2-(4-hydroxyphenyl)acetate (Journal of the Chemical Society [London] Part C, 1920 [1971]), using the procedure of Example 17.

EXAMPLE 19

6'-(2-Carboxy-2-phenylacetamido)penicillanoyloxymethyl Penicillanate 1,1-Dioxide To a stirred solution of 2.31 g. of 6'-aminopenicillanoyloxymethyl penicillanate 1,1-dioxide in 15 ml. of ethyl acetate is added 0.605 g. of N,N-dimethylaniline at 0° C. The temperature is maintained at 0° C., and 30 ml. of a 0.2 molar solution of phenylmalonyl chloride trimethylsilyl ester is added dropwise during 5 minutes. The reaction mixture is washed with water, and then an equal volume of fresh water is added. The pH of the aqueous phase is adjusted to 7.0 with saturated sodium bicarbonate and the layers are separated. The organic layer is discarded, and fresh ethyl acetate is added to the aqueous layer. The pH of the aqueous layer is lowered to 3.5, and again the layers are separated. The ethyl acetate layer is dried ($Na_2SO_4$) and evaporated in vacuo to give the title compound.

The 0.2 molar solution of phenylmalonyl chloride trimethylsilyl ester is prepared according to Preparation A of U.S. Pat. No. 3,862,933.

EXAMPLE 20

6'-(2-Carboxy-2-[3-thienyl]acetamido)penicillanoyloxymethyl Penicillanate 1,1-Dioxide The title compound is prepared by acylation of 6'-aminopenicillanoyloxymethyl penicillanate 1,1-dioxide with [3-thienyl]malonyl chloride trimethylsilyl ester, following the procedure of Example 19. [3-Thienyl]malonyl chloride trimethylsilyl ester is prepared according to the method of U.S. Pat. No. 3,862,933.

EXAMPLE 21

6'-(2-Carboxy-2-[2-thienyl]acetamido)penicillanoyloxymethyl Penicillanate 1,1-Dioxide The pH of a stirred suspension of 372 mg. of 2-[2-thienyl]malonic acid in 10 ml. of water and 5 ml. of tetrahydrofuran is adjusted to 6.0 by the addition of saturated sodium bicarbonate solution. To the resulting solution is added 923 mg. of 6'-aminopenicillanoyloxymethyl penicillanate 1,1-dioxide. The mixture is cooled to ca. 0° C., and 402 mg. of N-ethyl-N'-3-(dimethylamino)propylcarbodiimide hydrochloride is added, with stirring. Stirring is continued at ca 0° C. for 5 minutes and at 25° C. for 2 hours, the pH continuously being maintained between 5.8 and 6.0. At this point, the bulk of the tetrahydrofuran is removed by evaporation in vacuo, ethyl acetate and additional water are added and the pH is raised to 8.0. The layers are separated and the organic layer is discarded. Fresh ethyl acetate is added, and the pH is lowered to 3.0. Again the layers are separated, and the ethyl acetate layer is dried ($Na_2SO_4$) and evaporated in vacuo. This affords the title compound.

EXAMPLE 22

6'-(2-[4-Ethyl-2,3-dioxopiperazinocarbonylamino]-2-phenylacetamido)penicillanoyloxymethyl Penicillanate 1,1-Dioxide To a stirred mixture of 3.19 g. of 2-(4-ethyl-2,3-dioxopiperazinocarbonylamino)-2-phenylacetic acid in 50 ml. of acetone is added 1.2 ml. of N-methylmorpholine. The resulting mixture is cooled to −20° C., and a solution of 1.09 g. of ethyl chloroformate in 20 ml. of acetone is added dropwise during 10 minutes. Stirring is continued at −20° C. for 60 minutes, and then a solution of 4.61 g. of 6'-aminopenicillanoyloxymethyl penicillanate 1,1-dioxide in 50 ml. of acetone is added dropwise at −20° C. Stirring is continued at −20° C. for 60 minutes, at 0° C. for 30 minutes and at 25° C. for 30 minutes. At this point the solvent is removed by evaporation in vacuo, and the residue is partitioned between ethyl acetate and water at pH 2.5. The layers are separated and the aqueous layer is discarded. Fresh water is added and the pH is raised to 8.5. The layers are shaken and separated, and then the organic layer is discarded. Fresh ethyl acetate is added and the pH is again adjusted to 2.5. The layers are shaken and separated. The ethyl acetate layer is washed with water, and then it is dried. Evaporation of the ethyl acetate layer in vacuo affords the title compound.

EXAMPLE 23

The procedure of Example 22 is repeated, except that the 2-(4-ethyl-2,3-dioxopiperazinocarbonylamino)-2-phenylacetic acid is replaced by:
2-(2-oxoimidazolidinocarbonylamino)-2-phenylacetic acid,
2-(3-acetyl-2-oxoimidazolidinocarbonylamino)-2-phenylacetic acid,
2-(3-butyryl-2-oxoimidazolidinocarbonylamino)-2-phenylacetic acid,
2-(3-methylsulfonyl-2-oxoimidazolidinocarbonylamino)-2-phenylacetic acid and
2-(3-isopropylsulfonyl-2-oxoimidazolidinocarbonylamino)-2-phenylacetic acid,
respectively. This affords:
6'-(2-[2-oxoimidazolidinocarbonylamino]-2-phenylacetamido)penicillanoyloxymethyl penicillanate 1,1-dioxide,
6'-(2-[3-acetyl-2-oxoimidazolidinocarbonylamino-2-phenylacetamido)penicillanoyloxymethyl penicillanate 1,1-dioxide,
6'-(2-[3-butyryl-2-oxoimidazolidinocarbonylamino]2-phenylacetamido)penicillanoyloxymethyl penicillanate 1,1-dioxide,
6'-(2-[3-methylsulfonyl-2-oxoimidazolidinocarbonylamino]-2-phenylacetamido)penicillanoyloxymethyl penicillanate 1,1-dioxide and
6'-(2-[3-isopropylsulfonyl-2-oxoimidazolidinocarbonylamino]-2-phenylacetamido)penicillanoyloxymethyl penicillanate 1,1-dioxide,
respectively.

EXAMPLE 24

6'-Aminopenicillanoyloxymethyl Penicillanate 1,1-Dioxide

To a solution of 1.2 g. of 6'-(4-nitrobenzyloxycarbonylamino)penicillanoyloxymethyl penicillanate 1,1-dioxide in a mixture of 30 ml. of water and 50 ml. of tetrahydrofuran was added 1 drop of acetic acid (pH dropped to 4.5), followed by 1.2 g. of 10% palladium-on-carbon. The mixture was shaken under an atmosphere of hydrogen, at ca. 50 psig pressure, for 1.5 hours. The mixture was then filtered and the residue was washed with water and with tetrahydrofuran. The tetrahydrofuran-water, water and tetrahydrofuran solutions were combined and the pH was adjusted to 8.5. The resulting solution was extracted with ethyl acetate, and the ethyl acetate extract was dried ($Na_2SO_4$). The dried solution was evaporated in vacuo giving 600 mg. of crude material.

The crude material was chromatographed on silica gel, eluting with 3:1 ethyl acetate-hexane, which afforded 200 mg. of the title compound (23% yield). The IR spectrum (KBr disc) showed an absorption at 1783 $cm^{-1}$. The NMR spectrum ($CDCl_3$) showed absorptions at 5.9 (s), 5.5 (m), 4.63 (m,), 4.5 (s), 3.5 (d), 1.7 (s), 1.6 (s), 1.5 (s) and 1.45 (s) ppm.

6'-Aminopenicillanoyloxymethyl penicillanate 1,1-dioxide will form acid-addition salts. The salts are prepared in conventional fashion, i.e. using the methods described earlier for the formation of acid-addition salts of those compounds of formula I which have an amino group as part of the group $R^1$.

EXAMPLE 25

Chloromethyl Penicillanate 1,1-Dioxide

To a stirred solution of 24 g. of penicillanic acid 1,1-dioxide in 125 ml. of N,N-dimethylformamide was added 9.5 ml. of diisopropylethylamine, followed by 45 ml. of chloroiodomethane. Stirring was continued overnight and then the reaction mixture was added to 300 ml. of water. The pH was adjusted to 8.5, and then the mixture was extracted with ethyl acetate. The extract was washed with water, followed by saturated sodium chloride solution, and then it was dried over sodium sulfate. The dried extract was concentrated to dryness in vacuo to give the crude product as a gum (8.9 g.).

The crude product was combined with some additional material of comparable quality, and it was chromatographed on silica gel eluting with 1:1 ethyl acetate-hexane. This afforded the title compound which showed only a single spot when assayed by thin-layer chromatography. The IR spectrum (KBr disc) showed an absorption at 1801 cm$^{-1}$. The NMR spectrum (CDCl$_3$) showed absorptions at 6.0 (d, 1H, J=6 Hz), 5.7 (d, 1H, J=6 Hz), 4.7 (t, 1H, J=3.5 Hz), 4.5 (s, 1H), 3.55 (d, 2H, J=3.5 Hz), 1.7 (s, 3H) and 1.5 (s, 3H) ppm.

EXAMPLE 26

The procedure of Example 25 is repeated, except that the chloroiodomethane used therein is replaced by an equimolar amount of bromoiodomethane, diiodomethane, di(methylsulfonyloxy)methane, di(isobutylsulfonyloxy)methane, di(benzenesulfonyloxy)methane and di(4-toluenesulfonyloxy)methane. This affords:
bromomethyl penicillanate 1,1-dioxide,
iodomethyl penicillanate 1,1-dioxide,
methylsulfonyloxymethyl penicillanate 1,1-dioxide,
isobutylsulfonyloxymethyl penicillanate 1,1-dioxide,
benzenesulfonyloxymethyl penicillanate 1,1-dioxide and
4-toluenesulfonyloxymethyl penicillanate 1,1-dioxide, respectively.

EXAMPLE 27

Chloromethyl 6-(2-Benzyloxycarbonylamino-2-phenylacetamido)-penicillanate

To a 1 liter 3-neck round bottom flask equipped with a magnetic stirrer and containing 6-(2-benzyloxycarbonylamino-2-phenylacetamido)penicillanic acid (99.30 g.) in dimethylsulfoxide (500 ml.) cooled to 15° C. was added dropwise over a 15 minute period triethylamine (28.5 ml.). To this solution was added potassium iodide (2.0 g.) followed by the dropwise addition of iodochloromethane (143 g.) over a 15 minute period. The reaction was stirred at room temperature overnight. To this solution was added ethyl acetate (1 liter). The resultant organic layer was washed with brine (3×300 ml.) and water (1×300 ml.). The combined aqueous wash was reextracted with ethyl acetate (300 ml.). The ethyl acetate extracts were dried over magnesium sulfate, filtered and concentrated to afford 116 g. of crude product. Silica gel (1 kg.) chromatography using chloroform afforded 24.6 g. (23%) of the title compound as a light yellow foam, m.p. 75–77° C.

EXAMPLE 28

6'-(2-Benzyloxycarbonylamino-2-phenylacetamido)-penicillanoyloxymethyl Penicillanate 1,1-Dioxide To a 500 ml. round bottom flask equipped with a paddle stirrer and containing chloromethyl 6-(2-benzyloxycarbonylamino-2-phenylacetamido)penicillanate (20 g.) in dimethylsulfoxide (120 ml.) at room temperature was added sodium penicillanate 1,1-dioxide (9.6 g.) followed by potassium iodide (600 mg.). The reaction was allowed to stir overnight. An additional charge (2.4 g.) of sodium penicillanate 1,1-dioxide was added and the reaction mixture was stirred for an additional 6 hours. The crude reaction mixture was then poured into ice water (600 ml.) and extracted with ethyl acetate (1×500 ml., 3×200 ml.). The organic extracts were backwashed with water (2×500 ml.) and brine (1×500 ml.) and dried over magnesium sulfate in the presence of activated carbon. The solution was filtered and concentrated in vacuo to afford 23.9 g. of crude product. Silica gel (250 g.) chromatography using chloroform afforded 14.5 g. (53) of the title product, m.p. 80°–112° C.

EXAMPLE 29

6'-(2-Amino-2-phenylacetamido)penicillanoyloxymethyl Penicillanate 1,1-Dioxide Hydrochloride To a 500 ml. hydrogenation flask, containing 6'-2-benzyloxycarbonylamino-2-phenylacetamido)penicillanoyloxymethyl penicillanate 1,1-dioxide (5.50 g.) in tetrahydrofuran (75 ml.) were added water (75 ml.) acetic acid (1 drop) and 10% palladium on carbon (13.75 g.). The mixture was purged with nitrogen and then it was shaken under an atmosphere of hydrogen at 47 psig pressure for 30 minutes. An additional catalyst charge (3.00 g.) was added and the mixture was hydrogenated for an additional 15 minutes. The mixture was purged with nitrogen and filtered through a celite pad. The catalyst was washed with tetrahydrofuran (50 ml.) and water (30 ml.). The black solution was refiltered. 1.0N Hydrochloric acid (7.54 ml.) was then added to the aqueous solution which was cooled to 0° C. The pH of this yellow solution was 1.7. Tetrahydrofuran was then removed in vacuo and the resultant aqueous solution was saturated with sodium chloride and extracted with ether (2×100 ml.). The aqueous solution was then reextracted with methylene chloride (5×50 ml.). The organic extracts were backwashed with saturated brine (2×50 ml.), dried over magnesium sulfate and concentrated to ca. 100 ml. The crude product was precipitated with hexane (100 ml.) and filtered to afford 3.2 g. of a cream colored solid. The crude product was redissolved in methylene chloride (50 ml.) and precipitated slowly with hexane (40 ml.) to afford after drying (23°/1.6 mm.) 2.78 g. (58%) of the title product, m.p. 190° C.

PREPARATION 1

6-(2-Benzyloxycarbonylamino-2-phenylacetamido)-penicillanic Acid

To a mixture of 100 ml. of water and 50 ml. of tetrahydrofuran was added 10.1 g. of 6-(2-amino-2-phenylacetamido)penicillanic acid trihydrate and then the pH was adjusted to 8.0. To the solution so obtained was added benzyl chloroformate (3.6 ml.), dropwise, with stirring, at a pH of 8.0–8.5. Stirring was continued until the pH became stable, and then the solution was extracted with ethyl acetate. The ethyl acetate extract was discarded, and the pH of the aqueous phase was lowered to 2.0. The acidified aqueous phase was extracted with ethyl acetate, and the latter organic phase was dried and evaporated in vacuo. This afforded 11.4 g. of the title compound (94% yield). The NMR spectrum (CDCl$_3$/DMSO-d$_6$) showed absorptions at 8.2 (d, 1H), 7.6–7.2 (m, 10H), 7.0–6.6 (m, 1H), 5.6–5.3 (m, 3H), 5.1 (s, 2H), 4.3 (s, 1H) and 1.5 (2 s's, 6H) ppm.

PREPARATION 2

6-(2-Benzyloxycarbonylamino-2-[4-hydroxyphenyl]acetamido)penicillanic Acid

The title compound was prepared from 6-(2-amino-2-[4-hydroxyphenyl]acetamido)penicillanic acid and benzyl chloroformate, using the procedure of Preparation 1. Yield 97%. The NMR spectrum of the product (CDCl$_3$/DMSO-d$_6$) showed absorptions at 7.6–7.0 (m, 8H), 7.0–6.6 (d, 2H, J=8 Hz), 5.6–5.2 (m, 3H), 5.2–5.0 (s, 2H) and 1.5 (broad s, 6H) ppm.

PREPARATION 3

6-(2-[4-Nitrobenzyloxycarbonylamino]-2-phenylacetamido)penicillanic Acid

The title compound was prepared from 6-(2-amino-2-phenylacetamido)penicillanic acid and 4-nitrobenzyl chloroformate, using the procedure of Preparation 1.

The product thus obtained was partitioned between ethyl acetate and water and the pH was adjusted to 8.5 using potassium hydroxide. The ethyl acetate layer was removed and discarded, and the aqueous phase was lyophilized. This afforded the potassium salt of the title compound. Yield 82%. The NMR spectrum (CDCl$_3$/DMSO-d$_6$) showed absorptions at 8.2 (d, 2H, J=8 Hz), 7.8–7.2 (m, 7H), 5.8–5.4 (m, 3H), 5.2 (s, 2H), 4.2 (s, 1H), 4.0–3.6 (broad s, 2H) and 1.8–1.2 (m, 6H) ppm.

PREPARATION 4

6-(2-[4-Nitrobenzyloxycarbonylamino]-2-[4-hydroxyphenyl]acetamido)penicillanic Acid The title compound was prepared from 6-(2-amino-2-[4-hydroxyphenyl]acetamido)penicillanic acid and 4-nitrobenzyl chloroformate, using the procedure of Preparation 1. The product was converted into its potassium salt using the method described in Preparation 3.

PREPARATION 5

Chloromethyl 6-(2-Benzyloxycarbonylamino-2-phenylacetamido)penicillanate

A mixture of 1.04 g. of potassium 6-(2-benzyloxycarbonylamino-2-phenylacetamido)penicillanate, 0.87 ml. of chloroiodomethane and 10 ml. of N,N-dimethylformamide was stirred at ambient temperature overnight. The reaction mixture was poured into 50 ml. of water, and the pH was raised to 8.5. The acidified mixture was extracted with ethyl acetate. The extracts were combined, washed with water and then with saturated sodium chloride solution, and then they were dried (Na$_2$SO$_4$). Evaporation in vacuo gave 650 mg. (61% yield) of the title compound. The IR spectrum (KBr disc) showed an absorption at 1802 cm$^{-1}$. The NMR spectrum (CDCl$_3$) showed absorptions at 7.4 (s, 10H), 7.3–7.0 (m, 2H), 6.3 (d, 1H, J=7 Hz), 6.0–5.2 (m, 5H), 5.1 (s, 1H), 4.4 (s, 1H) and 1.5 (m, 6) ppm.

PREPARATION 6

Chloromethyl 6-(2-[4-Nitrobenzyloxycarbonylamino]-2-phenylacetamido)penicillanate The title compound was prepared from potassium 6-(2-[4-nitrobenzyloxycarbonylamino]-2-phenylacetamido)penicillanate and chloroiodomethane according to the procedure of Preparation 5. The yield of crude product was 68%.

A quantity (2.1 g.) of the above crude product was chromatographed on silica gel using 1:1 ethyl acetate-hexane as eluant, to give material showing only one spot when assayed by thin-layer chromatography.

PREPARATION 7

Chloromethyl 6-(2-[4-Nitrobenzyloxycarbonylamino]-2-[4-hydroxyphenyl]acetamido)penicillanate The title compound was prepared from potassium 6-(2-[4-nitrobenzyloxycarbonylamino]-2-[4-hydroxyphenyl]acetamido)penicillanate and chloroiodomethane according to the procedure of Preparation 5. The yield of crude product was 68%.

The crude product was chromatographed on silica gel using 2:1 ethyl acetate-hexane as eluant, to give a 29% yield of material showing only one spot when assayed by thin-layer chromatography. The NMR spectrum (CDCl$_3$) showed absorptions at 8.2 (d, 2H, J=8 Hz), 7.7–7.0 (m, 6H), 6.9–6.3 (m, 3H), 6.0–5.3 (m, 5H), 5.2 (s, 2H), 4.4 (s, 1H) and 1.5 (d, 6H) ppm.

PREPARATION 8

6'-(4-Nitrobenzyloxycarbonylamino)penicillanoyloxymethyl Penicillanate 1,1-Dioxide To a stirred solution of 4.32 g. of potassium 6-(4-nitrobenzyloxycarbonylamino)penicillanate in 60 ml. of dimethyl sulfoxide was added 2.53 g. of chloromethyl penicillanate 1,1-dioxide, followed by a few milligrams of sodium iodide. Stirring was continued for 16 hours, and then the mixture was poured in 200 ml. of water. The pH was adjusted to 8.5, and the resulting mixture was extracted with ethyl acetate. The ethyl acetate extracts were washed with water followed by saturated sodium chloride solution. The resulting solution was evaporated in vacuo to give 1.57 g. of crude material.

The crude material was chromatographed on silica gel, eluting with ethyl acetate, to give 1.2 g. of the title compound. The NMR spectrum showed absorptions at 8.25 (d), 7.50 (d), 5.95 (s), 5.73 (m), 5.55 (broad s), 5.23 (s), 4.75 (t), 4.46 (s), 4.44 (s), 3.46 (s), 3.44 (s), 1.72 (s), 1.65 (s), 1.52 (s) and 1.40 (s) ppm.

PREPARATION 9

6-(2-Benzyloxycarbonylamino-2-phenylacetamido)penicillanic Acid

To a 3 liter 3-neck round bottom flask equipped with a paddle stirrer and containing 6-(2-amino-2-phenylacetamido)penicillanic acid trihydrate (121.04 g.), tetrahydrofuran (550 ml.), and water (1000 ml.) cooled to 5° C. was added 10% sodium hydroxide (~108 ml.) until the pH was ~7.7. Over a 45 minute period with cooling, benzylchloroformate (53.87 g.) and 10% sodium hydroxide (~108 ml.) were simultaneously added while the pH was maintained between 8.0–8.5. The reaction mixture was stirred with cooling for an additional hour after completion of the addition. The crude reaction mixture was concentrated in vacuo to remove the tetrahydrofuran. The aqueous solution was extracted with ethyl acetate (2×250 ml.). This organic extract was discarded. The aqueous solution was cooled to 5° C., ethyl acetate (500 ml.) was added, and the pH was adjusted to 2.0 using 6N hydrochloric acid (50 ml.). The organic layer was separated and the aqueous was reextracted with ethyl acetate (3×250 ml.). The combined organic extracts were washed with brine (100 ml.), dried over magnesium sulfate, filtered and concentrated to afford crude product which was slurried with ether and filtered. The ether filtrate was concentrated to afford a white foam which was slurried with hexane and also filtered. The combined crude products were dried in vacuo overnight to yield 137.8 g. (95%) of the title compound, m.p. 144°–145° C.

I claim:

1. The 4-toluenesulfonate salt of 6'-(2-amino-2-phenylacetamido)penicillanoyloxymethyl penicillanate 1,1-dioxide.

* * * * *